(12) United States Patent
Giloh

(10) Patent No.: US 6,987,210 B1
(45) Date of Patent: *Jan. 17, 2006

(54) PROTECTIVE UNDERGARMENT

(75) Inventor: Tamar Giloh, Salford (GB)

(73) Assignee: TamiCare Ltd., (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/744,779

(22) PCT Filed: Aug. 5, 1999

(86) PCT No.: PCT/IL99/00434

§ 371 (c)(1),
(2), (4) Date: Jun. 6, 2002

(87) PCT Pub. No.: WO00/67468

PCT Pub. Date: Feb. 17, 2000

(30) Foreign Application Priority Data

Jul. 8, 1998 (IL) ..................................... 125695

(51) Int. Cl.
A61F 13/15 (2006.01)
A41B 9/00 (2006.01)

(52) U.S. Cl. ................. 604/373; 604/377; 604/385.07; 604/393; 2/400; 2/78.1

(58) Field of Classification Search ................ 604/373, 604/377, 381, 385.07, 393; 2/400, 403, 406, 2/73, 78.1–78.4, 113; 450/1–93

See application file for complete search history.

(56) References Cited

U.S. PATENT DOCUMENTS

| | | | |
|---|---|---|---|
| 2,796,064 A | 6/1957 | Green et al. ................. | 128/288 |
| 4,044,769 A | 8/1977 | Papajohn | |
| 4,560,381 A | 12/1985 | Southwell | |
| 4,589,876 A | 5/1986 | Van Tilburg | |
| 4,698,847 A * | 10/1987 | Yoshihara ........................ | 2/69 |
| 4,880,424 A | 11/1989 | Rautenberg | |
| 4,961,418 A | 10/1990 | McLaurin-Smith | ......... 128/157 |
| 5,098,419 A | 3/1992 | Gold | |
| 5,149,336 A | 9/1992 | Clarke et al. | |
| 5,685,874 A | 11/1997 | Buell et al. | |

(Continued)

FOREIGN PATENT DOCUMENTS

| | | |
|---|---|---|
| CH | 682288 | 8/1993 |
| CN | 1107279 | 8/1995 |
| DE | 187101 | 7/1907 |

(Continued)

OTHER PUBLICATIONS

Many Moons Alternative Menstruation Products Ecofem Page, pp. 1-4, Jun. 18, 1997.

Primary Examiner—Larry I. Schwartz
Assistant Examiner—C Lynne Anderson
(74) Attorney, Agent, or Firm—McDonnell Boehnen Hulbert & Berghoff LLP

(57) ABSTRACT

A protective undergarment including an integrally formed undergarment body formed of a liquid impermeable material, and an absorptive pad associated with the integrally formed undergarment body.

47 Claims, 4 Drawing Sheets

U.S. PATENT DOCUMENTS

| | | | |
|---|---|---|---|
| RE35,687 E | | 12/1997 | Igaue et al. |
| 5,758,367 A | * | 6/1998 | Torrent Lopez et al. ........ 2/400 |
| 5,800,245 A | * | 9/1998 | Barbe-Vicuna et al. ....... 450/57 |
| 5,888,118 A | * | 3/1999 | Kishi .......................... 450/122 |
| 5,921,976 A | * | 7/1999 | Seymore ................ 604/385.03 |
| 6,060,638 A | * | 5/2000 | Paul et al. ................... 604/378 |
| 6,365,794 B1 | * | 4/2002 | Dabi et al. .................. 604/367 |
| 6,502,250 B2 | * | 1/2003 | Suga et al. ..................... 2/406 |

FOREIGN PATENT DOCUMENTS

| | | |
|---|---|---|
| DE | 19704603 | 1/1998 |
| EP | 0 327 823 | 8/1992 |
| EP | 0 737 462 A1 | 4/1995 |
| EP | 1 136 050 A1 | 7/2000 |
| GB | 1 356 465 | 6/1974 |
| WO | WO 96/36248 | 11/1996 |
| WO | WO 97/21411 | 6/1997 |
| WO | WO 97/30671 | 8/1997 |
| WO | WO 00/07468 | 2/2000 |

* cited by examiner

US 6,987,210 B1

PROTECTIVE UNDERGARMENT

FIELD OF THE INVENTION

The present invention relates to protective undergarments generally as well as to methods for manufacture thereof.

BACKGROUND OF THE INVENTION

Various types of protective undergarments are known in the patent literature. The following patents and patent applications and the references cited therein are believed to represent the state of the art: U.S. Pat. No. 5,098,419; PCT Published Patent Application WO 96/36248 and European Patent 327,823.

SUMMARY OF THE INVENTION

The present invention seeks to provide a protective undergarment which is generally lighter and more comfortable than conventional protective undergarments and which can be manufactured in large quantities at relatively low cost.

There is thus provided in accordance with a preferred embodiment of the present invention a protective undergarment including an integrally formed undergarment body formed of a liquid impermeable material, and an absorptive pad associated with the integrally formed undergarment body.

Preferably, the undergarment body includes a first portion which is formed with multiple perforations to permit passage of perspiration therethrough, and a second portion which is substantially not perforated, so as to prevent passage of body fluids therethrough.

In accordance with a preferred embodiment of the present invention the absorptive pad is associated with the undergarment body at the second portion.

Preferably, the second portion extends beyond the absorptive pad.

There is additionally provided in accordance with a preferred embodiment of the present invention a protective undergarment comprising an integrally formed undergarment body formed of a liquid impermeable material, the undergarment body including a first portion which is formed with multiple perforations to permit passage of perspiration therethrough, and a second portion which is substantially not perforated, so as to prevent passage of body fluids therethrough.

Preferably, the liquid impermeable material is latex.

Alternatively, the liquid impermeable material is silicone rubber.

In accordance with a preferred embodiment of the present invention, the undergarment body has a thickness of approximately 10 microns.

Preferably, the protective garment also comprises an absorbent pad fixed to the undergarment body.

The protective undergarment may be a brassiere, underpants or any other suitable garment.

The protective undergarment may have fibers adhered to at least one surface of the undergarment body.

In accordance with one embodiment of the present invention, the absorbent pad includes a portion extending downward from the crotch along the thigh.

There is additionally provided in accordance with a preferred embodiment of the present invention a method of manufacture of protective undergarments comprising the steps of forming an undergarment body of a liquid impermeable material, and forming multiple perforations on a first portion of the undergarment body to permit passage of perspiration therethrough.

Preferably, the step of associating an absorbent pad with a second portion of the undergarment body.

There is also provided in accordance with a preferred embodiment of the present invention a method of manufacture of protective undergarments comprising the steps of forming an undergarment body of a liquid impermeable material, and fixedly associating an absorbent pad with the undergarment body.

Preferably, the associating step comprising forming the undergarment body over a portion of the pad.

Preferably, the method also includes the step of forming the undergarment body over an absorbent pad, so as to fix the pad to the undergarment body.

Additionally in accordance with a preferred embodiment of the present invention, the method includes the step of adhering cotton fibers to at least one surface of the undergarment body.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENT

Reference is now made to FIGS. 1A, 1B, 1C, 1D, 1E, 1F, 1G, 1H and 1I are simplified illustrations of a method for producing protective undergarments in accordance with a preferred embodiment of the present invention. The invention is described hereinbelow with reference to FIGS. 1A–1I, with specific reference to underpants, it being appreciated that the invention applies equally to any other suitable undergarment.

Figure 1A:
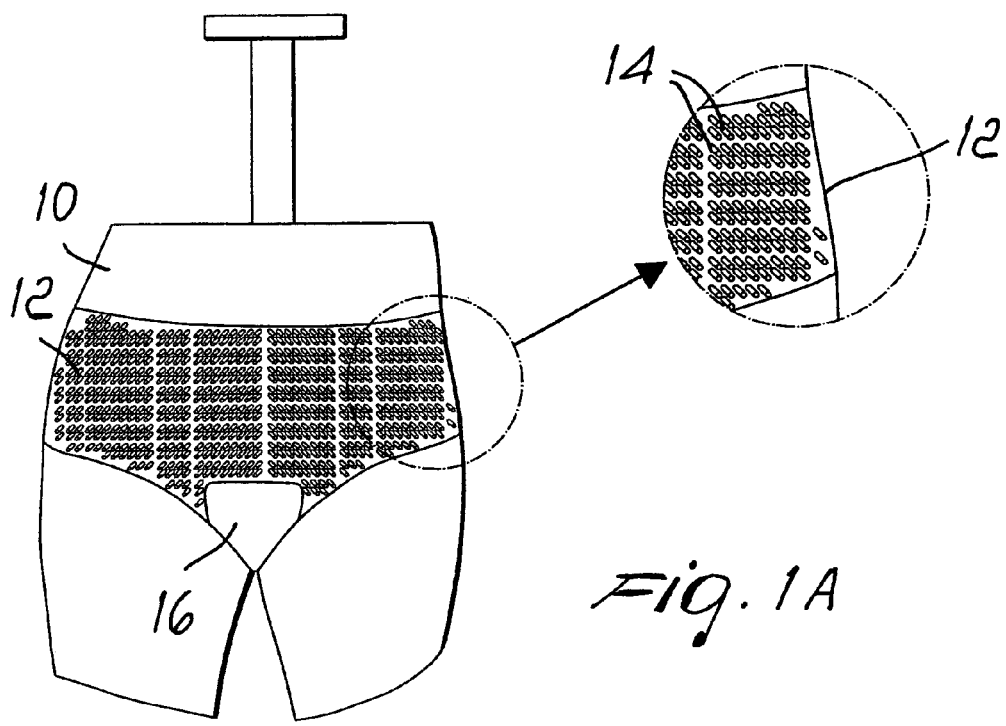
FIGS. 1A, 1B, 1C, 1D, 1E, 1F, 1G, 1H and 1I are illustrations of a method for producing protective undergarments in accordance with a preferred embodiment of the present invention.

As seen in FIG. 1A, a three dimensional garment form 10 is provided on which an array 12 of protrusions 14, such as needles, is formed in the general shape of underpants to be formed. The crotch area 16 of the underpants is preferably not formed with protrusions 14. The remainder of the form 10 is preferably coated with a non-adhesion substance, such as TEFLON R.

Figure 1B:
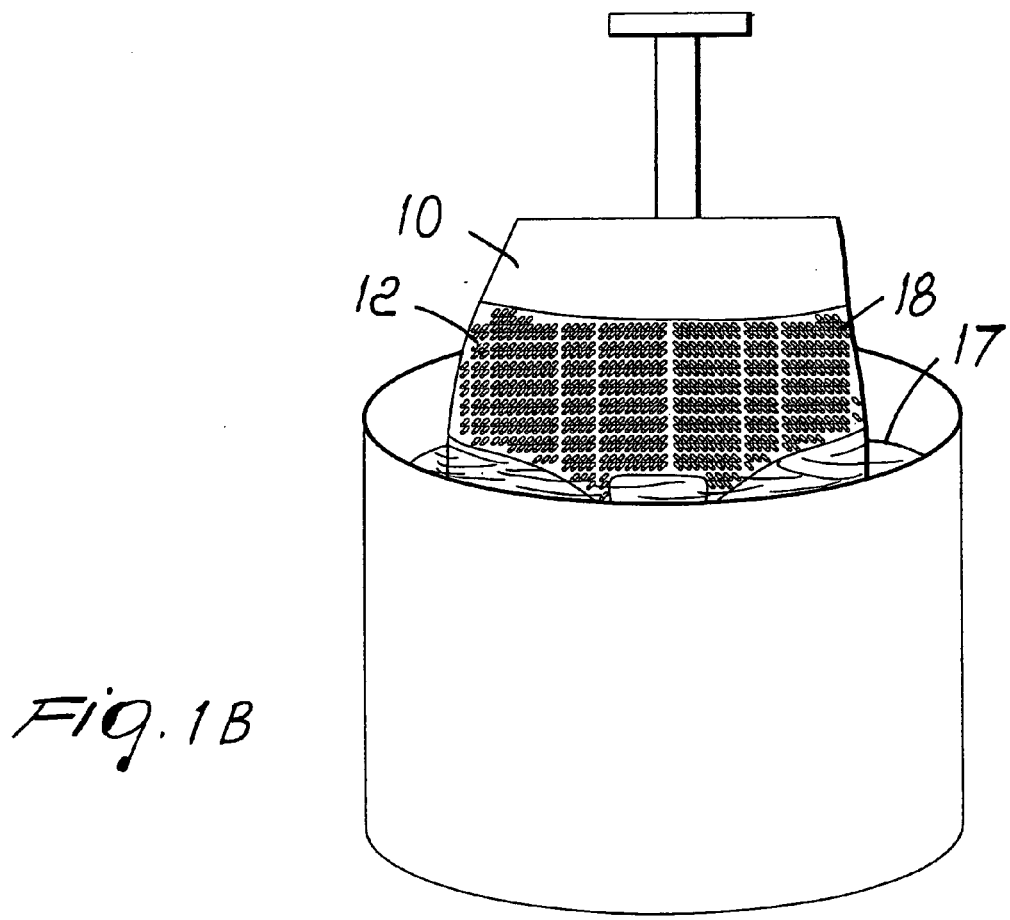

As shown in FIG. 1B, garment form 10 is preferably dipped in a liquid 18, such as latex or silicone, which when allowed to dry, forms a stretchable, light weight garment 18 over array 12 and crotch area 16. It may be appreciated that the provision of protrusions 14 causes the garment 18 to be perforated except at crotch area 16. Thus the garment 18 is "breathable" except at the crotch area 16, where it is liquid impermeable.

Figure 1C:
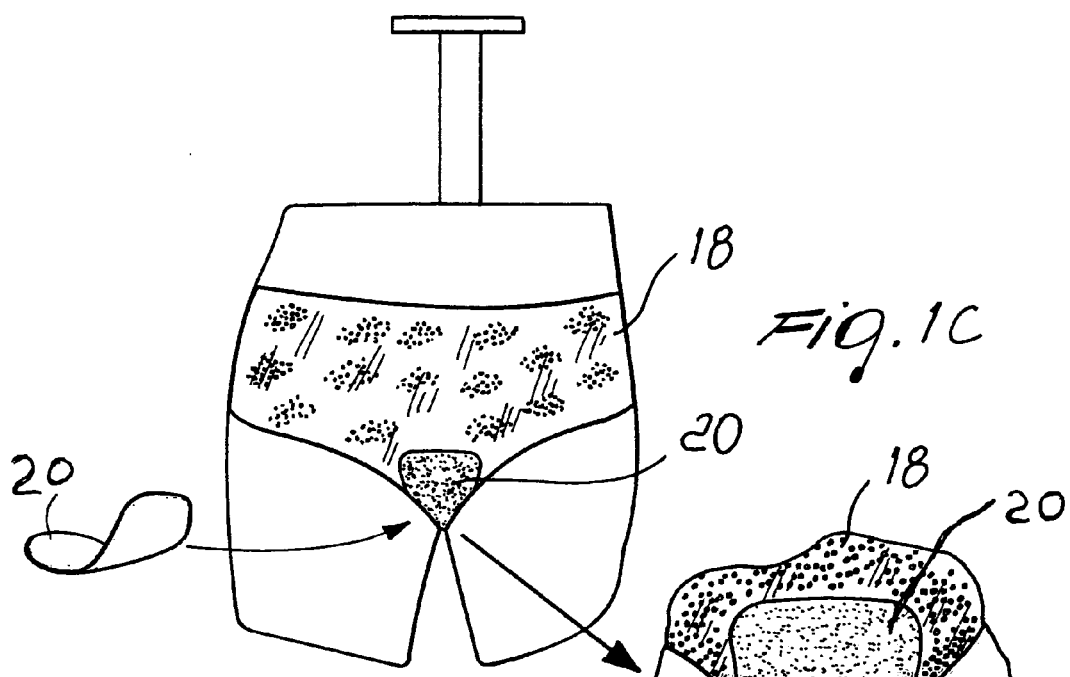

In accordance with a preferred embodiment of the present invention, as illustrated in FIG. 1C, an absorptive pad 20 is associated with the light weight garment 18 at the crotch area 16. It may be associated by the use of an adhesive, but is preferably attached to the remainder of garment 18 by virtue of the fact that the liquid is allowed to dry on the form 10 in engagement with the absorptive pad 20.

Figure 1D:
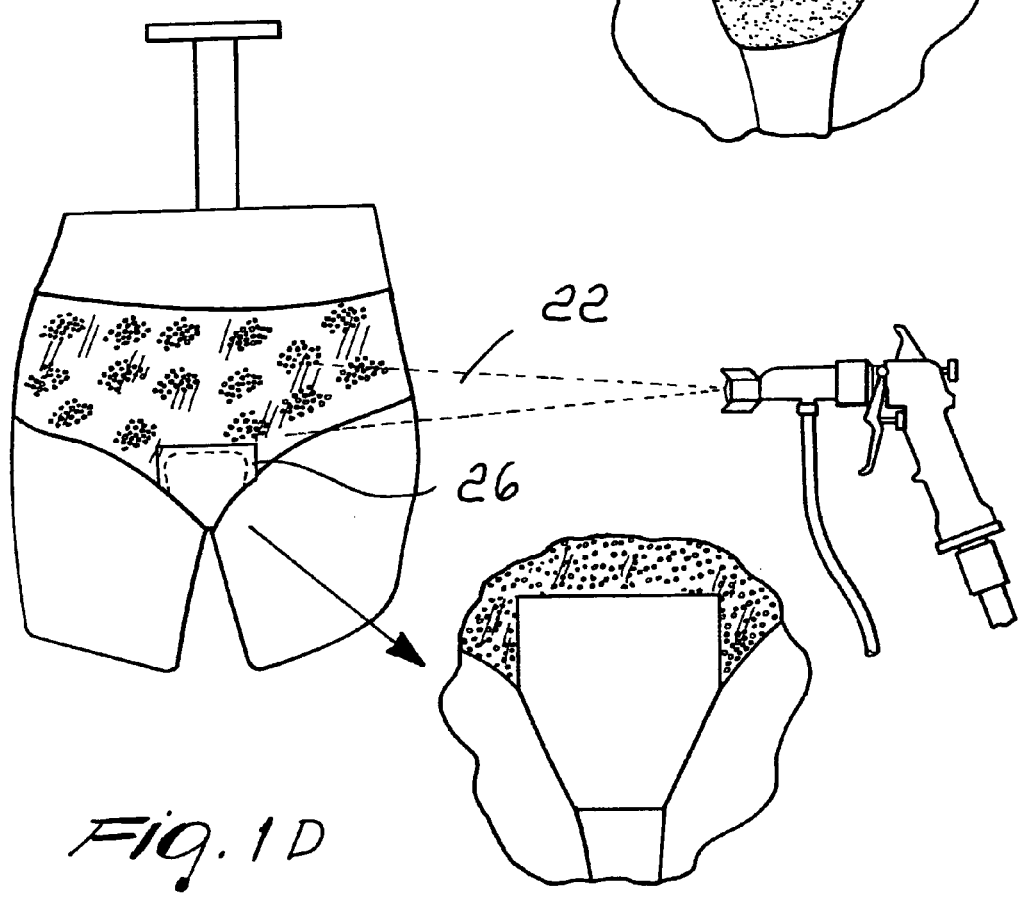
Figure 1E:
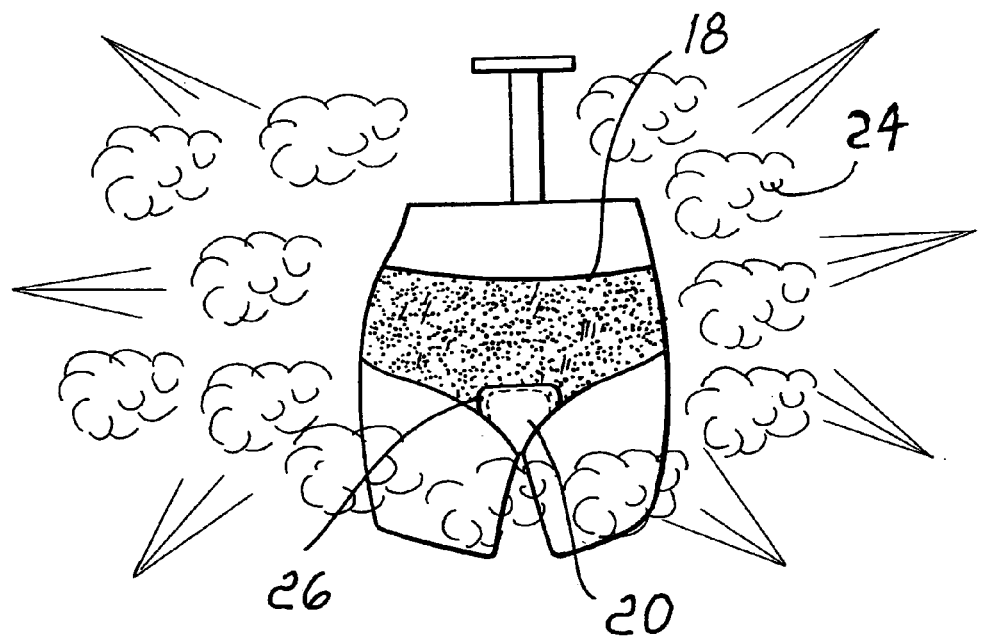

Prior to removal of the garment 18 from the form 10, the exterior surface of the garment on the form 10, which will eventually be turned inside-out to form the interior surface, is preferably sprayed with adhesive 22, as shown in FIG. 1D and thereafter with cotton fibers 24 or any other suitable material, as indicated in FIG. 1E, thereby to provide a comfortable and non-stick skin engaging surface. Preferably pad 20 is covered during the steps of FIGS. 1D and 1E with a cover 26, which extends somewhat beyond the pad, so as to prevent liquid migration from the pad to the cotton fibers.

Figure 1F:
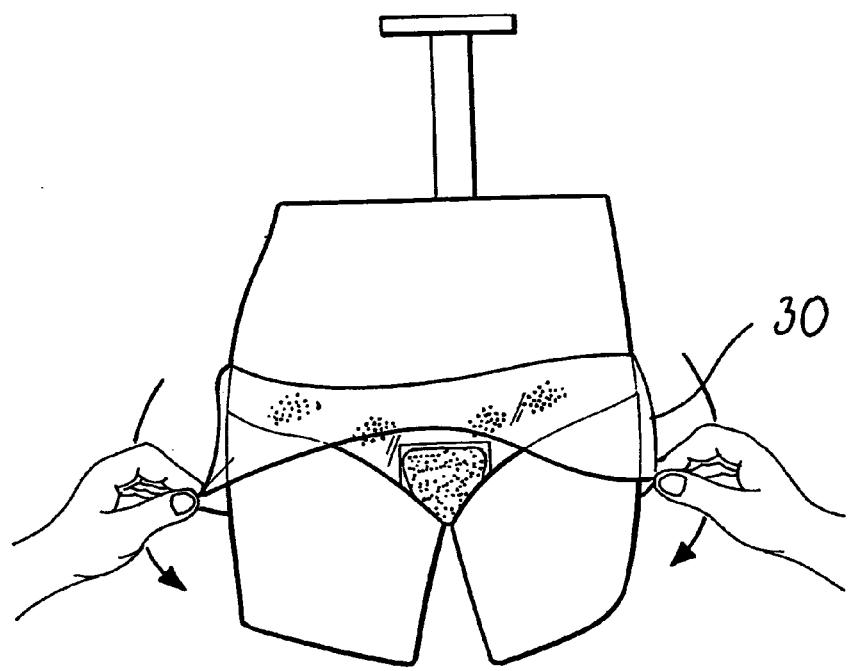

The resulting garment 30 may then be removed from the form 10, as seen in FIG. 1F and turned inside out. The outer surface of garment 30 may be coated or otherwise covered with cotton fiber or any other suitable material and finished in an appropriate manner.

Figure 1G:
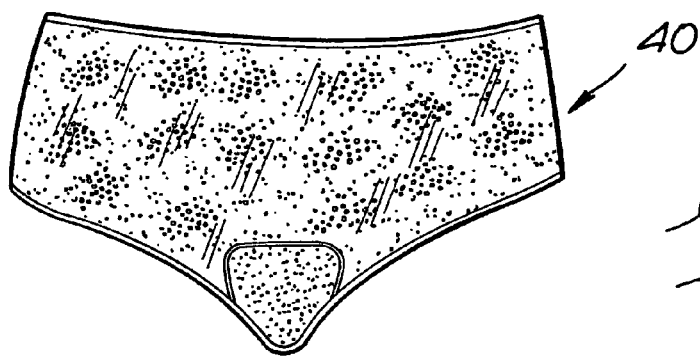
Figure 1H:
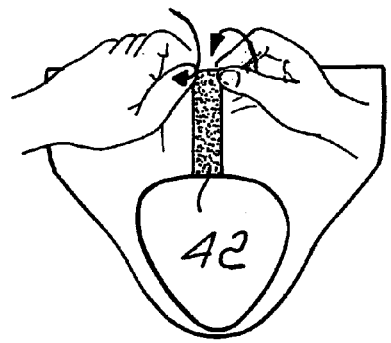
Figure 1I:
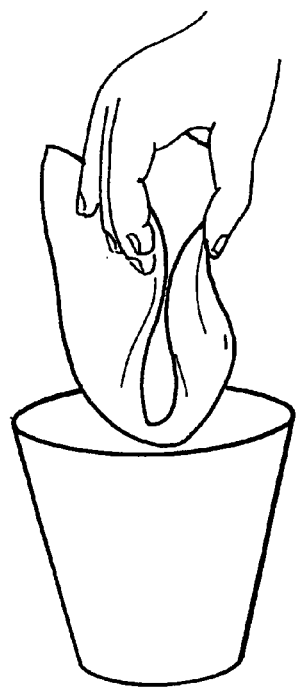

The completed garment 40, as seen in FIG. 1G, is preferably extremely light weight, low cost, stretchable, underpants, which is perforated generally except at the crotch area and which is preferably integrally formed with an internal absorptive pad at the crotch area. The garment is preferably formed of an elastic material, such as latex or silicone and has a thickness of less than 10 microns. In accordance with a preferred embodiment of the present invention, as seen in FIG. 1H, a tear region 42 may be incorporated in the garment, such as at a side thereof. This enables ease of removal of the garment, by tearing it at region 42. Once removed the torn, worn garment may be disposed of, as illustrated in FIG. 1I.

Figure 2:
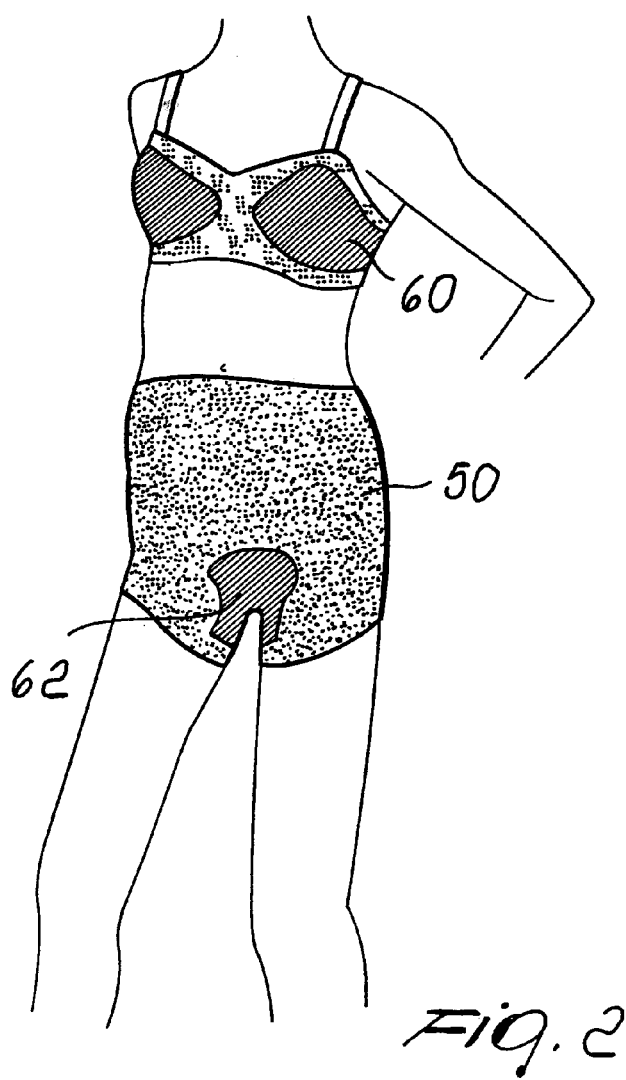
FIG. 2 is a simplified illustration of protective undergarments produced generally by the method of FIGS. 1A–1F in accordance with a preferred embodiment of the present invention.

As can be seen from FIG. 2, the garment may be underpants 50, a brassiere 60, or any other suitable garment. It is noted that the pad 62 of the underpants 50 may have a portion which extends downwardly along the wearer's legs.

It will be appreciated by persons skilled in the art that the present invention is not limited by what has been particularly shown and described hereinabove. Rather the scope of the present invention includes variations and modifications of the various features described in the specification and shown in the drawings which may occur to a person of ordinary skill in the art upon reading the foregoing description and which are not in the prior art.

What is claimed is:

1. Protective garment comprising:
   an integrally formed garment body of a liquid impermeable material having an inner surface with a first portion and a second portion;
   an absorptive device associated with the second portion of the inner surface of the integrally formed garment body; and
   loose fibres directly affixed to at least a substantial part of the first portion of the inner surface of the integrally formed garment body and proximate to the absorptive device.

2. A protective garment according to claim 1, wherein the fibres are affixed to the inner surface of the integrally formed garment body except for a section of the garment body associated with the absorptive device.

3. A protective garment according to claim 1, wherein said first portion is formed with multiple perforations to permit passage of perspiration therethrough.

4. A protective garment according to claim 3, wherein said second portion is not substantially perforated, so as to prevent passage of body fluids therethrough.

5. A protective garment according to claim 1, wherein the integrally formed garment body has an outer surface, and further comprising loose fibres directly affixed to at least a portion of the outer surface of the integrally formed garment body.

6. A protective garment according to claim 1, wherein the liquid impermeable material is rubber.

7. A protective garment according to claim 1, wherein the fibres are cotton.

8. A protective garment according to claim 1, wherein the second portion extends beyond said absorptive device.

9. A protective garment according to claim 1, wherein the garment is a body-tight seamless garment.

10. A protective garment according to claim 2, wherein the garment is a body-tight seamless garment.

11. A protective garment according to claim 1, wherein said garment is underpants.

12. A protective garment according to claim 1, wherein said garment is brassiere.

13. A method of manufacture of a protective garment comprising the steps of:
    forming an garment body of a liquid impermeable material, the garment body having an inner surface with a first portion and a second portion;
    associating an absorptive device with the second portion of the inner surface of the garment body; and
    affixing loose fibres directly to at least a substantial part of the first portion of the inner surface of the garment body and proximally to the absorptive device.

14. A method of manufacture of a protective garment according to claim 13, wherein the associating of the absorptive device with the second portion includes contacting the absorptive device while the liquid impermeable material is drying.

15. A method of manufacture of a protective garment according to claim 13, wherein the fibres are cotton.

16. A method of manufacture of a protective garment according to claim 13, wherein the affixing of fibres includes spraying an adhesive to the part of the first portion and spraying fibres to the part of the first portion.

17. A method of manufacture of a protective garment according to claim 13, wherein the affixing of fibres comprises affixed fibres to the inner surface of the garment body except for a section of the garment body associated with the absorptive device.

18. A method of manufacture of a protective garment according to claim 13, wherein the garment body has an outer surface, and further comprising affixing fibres directly to a part of the outer surface of the garment body.

19. A protective garment comprising:
    an integrally formed garment body of an elastic liquid impermeable material having an inner surface with a first portion and a second portion;
    an absorptive device associated with the second portion of the inner surface of the integrally formed garment body; and
    loose fibres directly affixed to at least a substantial part of the first portion of the inner surface of the integrally formed garment body and proximate to the absorptive device.

20. A protective garment according to claim 19, wherein the fibres are affixed to the inner surface of the integrally formed garment body except for a section of the garment body associated with the absorptive device.

21. A protective garment according to claim 19, wherein said first portion is formed with multiple perforations to permit passage of perspiration therethrough.

22. A protective garment according to claim 21, wherein said second portion is not substantially perforated, so as to prevent passage of body fluids therethrough.

23. A protective garment according to claim 19, wherein the integrally formed garment body has an outer surface, and further comprising fibres directly affixed to at least a portion of the outer surface of the integrally formed garment body.

24. A protective garment according to claim 19, wherein the liquid impermeable material is rubber.

25. A protective garment according to claim 19, wherein the fibres are cotton.

26. A protective garment according to claim 19, wherein the second portion extends beyond said absorptive device.

27. A protective garment according to claim 19, wherein the garment is a body-tight seamless garment.

28. A protective garment according to claim 20, wherein the garment is a body-tight seamless garment.

29. A method of manufacture of a protective garment comprising the steps of:
   forming an integral garment body of an elastic liquid impermeable material, the integral garment body having an inner surface with a first portion and a second portion;
   an absorptive device associated with the second portion of the inner surface of the integrally formed garment body; and
   affixing loose fibres directly to at least a substantial part of the first portion and proximally to the absorptive device.

30. A method of manufacture of a protective garment according to claim 29, wherein the associating of the absorptive device with the second portion includes contacting the absorptive device while the liquid impermeable material is drying.

31. A method of manufacture of a protective garment according to claim 29, wherein the fibres are cotton.

32. A method of manufacture of a protective garment according to claim 29, wherein the affixing of fibres includes spraying an adhesive to the part of the first portion and spraying fibres to the part of the first portion.

33. A method of manufacture of a protective garment according to claim 29, wherein the affixing of fibres comprises affixed fibres to the inner surface of the garment body except for a section of the garment body associated with the absorptive device.

34. A method of manufacture of a protective garment according to claim 29, wherein the garment body has an outer surface, and further comprising affixing fibres directly to a part of the outer surface of the garment body.

35. Protective garment comprising:
   an integrally formed garment body of a liquid impermeable material having an inner surface, the body formed with multiple perforations to permit perspiration therethrough; and
   loose fibres directly affixed to at least a substantial portion of the inner surface of the integrally formed garment body.

36. A protective garment according to claim 35 wherein the inner surface has a first portion and a second portion.

37. A protective garment according to claim 35, further comprising an absorptive device associated with the second portion of the inner surface of the integrally formed garment body.

38. A protective garment according to claim 37, wherein the fibres that are affixed to the first portion of the inner surface of the integrally formed garment body are proximate to the portion of the garment body associated with the absorptive device.

39. A protective garment according to claim 37 wherein said second portion is not substantially perforated, so as to prevent passage of body fluids therethrough.

40. A protective garment according to claim 35, wherein the integrally formed garment body has an outer surface, and further comprising fibres directly affixed to at least a portion of the outer surface of the integrally formed garment body.

41. A protective garment according to claim 35, wherein the liquid impermeable material is rubber.

42. A protective garment according to claim 35, wherein the fibres are cotton.

43. A protective garment according to claim 37, wherein the second portion extends beyond said absorptive device.

44. A protective garment according to claim 35, wherein the garment is a body-tight seamless garment.

45. A protective garment according to claim 37, wherein the garment is a body-tight seamless garment.

46. A protective garment according to claim 35, wherein said garment is underpants.

47. A protective garment according to claim 35, wherein said garment is brassiere.

\* \* \* \* \*